United States Patent
Lee et al.

(10) Patent No.: US 10,604,418 B2
(45) Date of Patent: Mar. 31, 2020

(54) POROUS OXIDE SEMICONDUCTOR INCLUDING THREE-DIMENSIONALLY INTERCONNECTED NANOPORES, MESOPORES, AND MACROPORES, METHOD FOR PREPARING THE POROUS OXIDE SEMICONDUCTOR AND GAS SENSOR INCLUDING THE POROUS OXIDE SEMICONDUCTOR AS GAS SENSING MATERIAL

(71) Applicant: Korea University Research and Business Foundation, Seoul (KR)

(72) Inventors: Jong Heun Lee, Seoul (KR); Yun Chan Kang, Seoul (KR); Jee-Uk Yoon, Zurich (CH); Seung Ho Choi, Gyeonggi-do (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 15/747,698

(22) PCT Filed: Jun. 30, 2016

(86) PCT No.: PCT/KR2016/006997
§ 371 (c)(1),
(2) Date: Jan. 25, 2018

(87) PCT Pub. No.: WO2017/018674
PCT Pub. Date: Feb. 2, 2017

(65) Prior Publication Data
US 2018/0215628 A1    Aug. 2, 2018

(30) Foreign Application Priority Data
Jul. 28, 2015 (KR) .................. 10-2015-0106544

(51) Int. Cl.
C01G 41/02 (2006.01)
C01G 1/02 (2006.01)
(Continued)

(52) U.S. Cl.
CPC .............. *C01G 41/02* (2013.01); *C01B 13/34* (2013.01); *C01G 1/02* (2013.01); *C01G 19/02* (2013.01);
(Continued)

(58) Field of Classification Search
CPC .......... C01G 41/02; C01G 1/02; C01G 19/02; C01B 13/34; G01N 27/127; G01N 27/40
See application file for complete search history.

(56) References Cited

U.S. PATENT DOCUMENTS

| 2011/0092363 A1* | 4/2011 | Seo ........................ C01B 13/324 502/415 |
| 2013/0048568 A1* | 2/2013 | Le ............................ C22B 3/24 210/682 |

FOREIGN PATENT DOCUMENTS

| KR | 20060108909 A | 10/2006 |
| KR | 20070066859 A | 6/2007 |
(Continued)

OTHER PUBLICATIONS

Hyodo et al., "No2 sensing properties of macroporous In2O3-based powders fabricated by utilizing ultrasonic spray pyrolysis emplying polymehtylmethacrylate microspheres as a template," Sensors and Actuators B (2010); 151:265-273.
(Continued)

Primary Examiner — James A Fiorito
(74) Attorney, Agent, or Firm — Fox Rothschild LLP

(57) ABSTRACT

The present invention relates to a porous oxide semiconductor including three-dimensionally interconnected nanopores, mesopores, and macropores, a method for preparing
(Continued)

the porous oxide semiconductor, and a gas sensor including the porous oxide semiconductor as a gas sensing material. The nanopores have a diameter of 1 nm to less than 4 nm, the mesopores have a diameter of 4 nm to 50 nm, and the macropores have a diameter of 100 nm to less than 1 μm. The oxide semiconductor gas sensor of the present invention exhibits ultrahigh response and ultrafast response to various analyte gases due to the presence of the controlled nanopores, mesopores, and macropores.

3 Claims, 18 Drawing Sheets

(51) Int. Cl.
 *C01B 13/34* (2006.01)
 *G01N 27/12* (2006.01)
 *G01N 27/40* (2006.01)
 *C01G 19/02* (2006.01)

(52) U.S. Cl.
 CPC ........... *G01N 27/127* (2013.01); *G01N 27/40* (2013.01); *C01P 2004/03* (2013.01); *C01P 2004/04* (2013.01); *C01P 2004/62* (2013.01); *C01P 2006/12* (2013.01); *C01P 2006/16* (2013.01); *C01P 2006/17* (2013.01); *G01N 27/126* (2013.01)

(56) References Cited

FOREIGN PATENT DOCUMENTS

| KR | 100838644 B1 | 6/2008 |
|---|---|---|
| KR | 100924214 B1 | 10/2009 |
| KR | 101255217 B1 | 4/2013 |

OTHER PUBLICATIONS

Qin et al., "Hierarchically Porous CuO Hollow Spheres Fabricated via a One-Pot Template-Free Method for High-Performance Gas Sensors," The Journal of Physical Chemistry (2012): 116:11994-12000.

* cited by examiner

[Fig. 1]
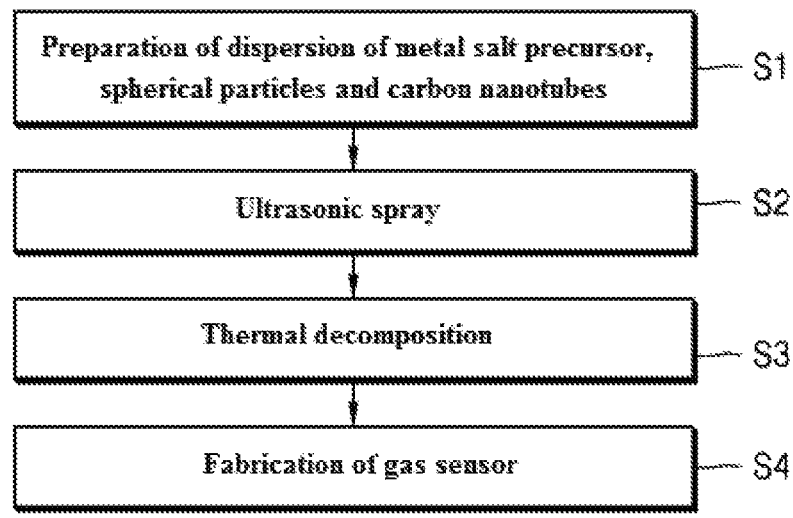
[Fig. 2a]
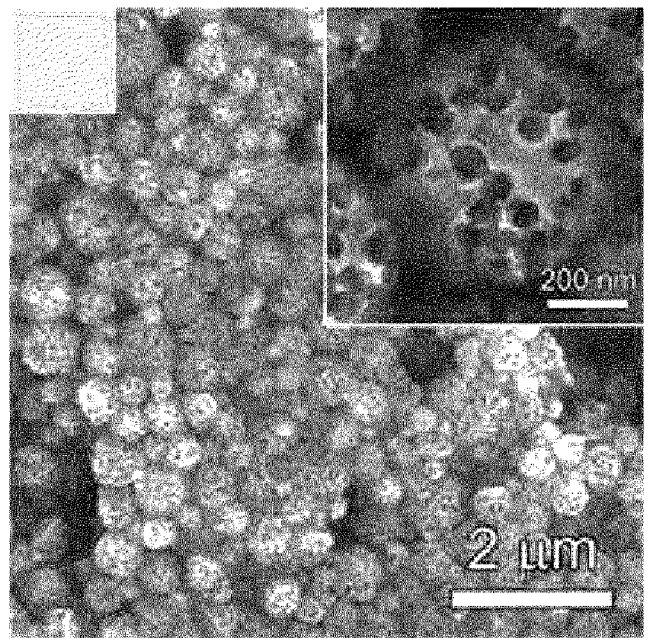

[Fig. 2b]
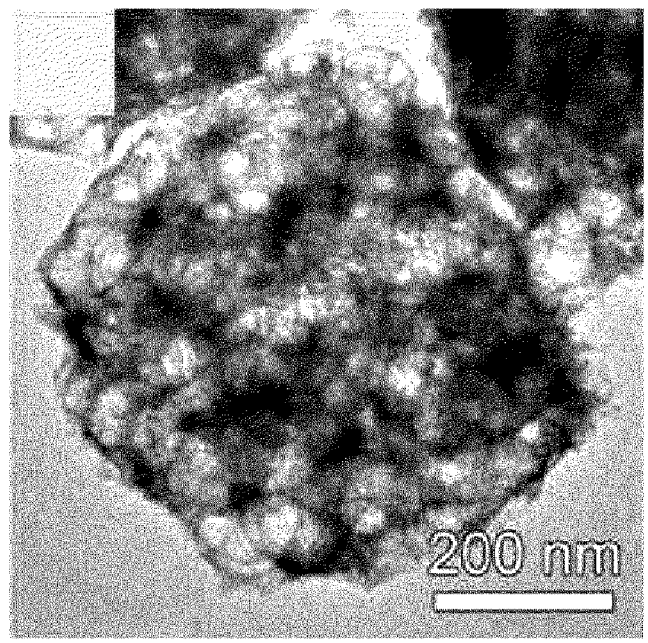
[Fig. 2c]
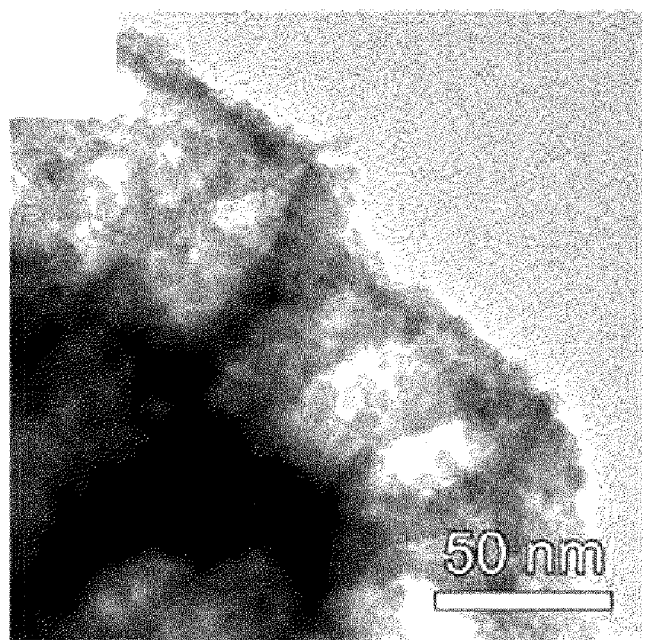

[Fig. 2d]
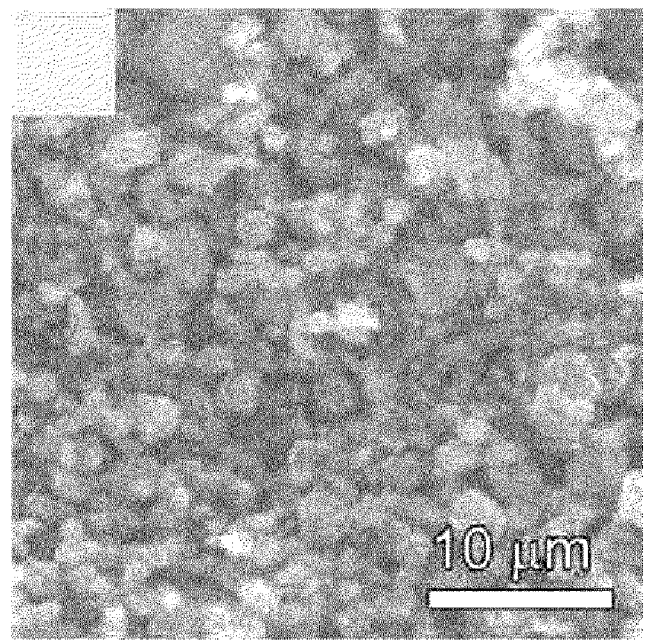
[Fig. 2e]
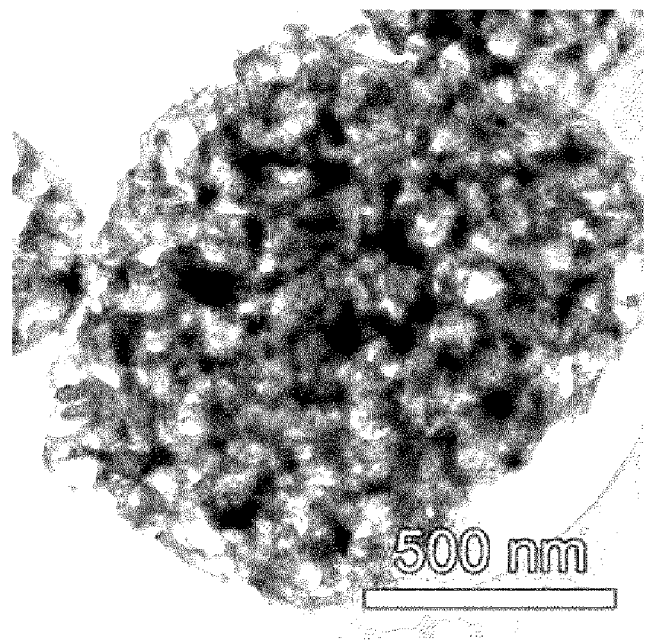

[Fig. 3a]
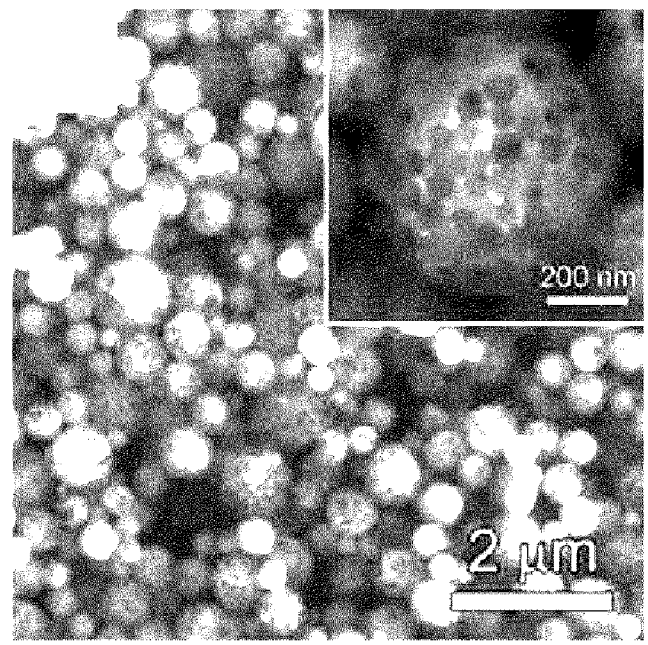
[Fig. 3b]
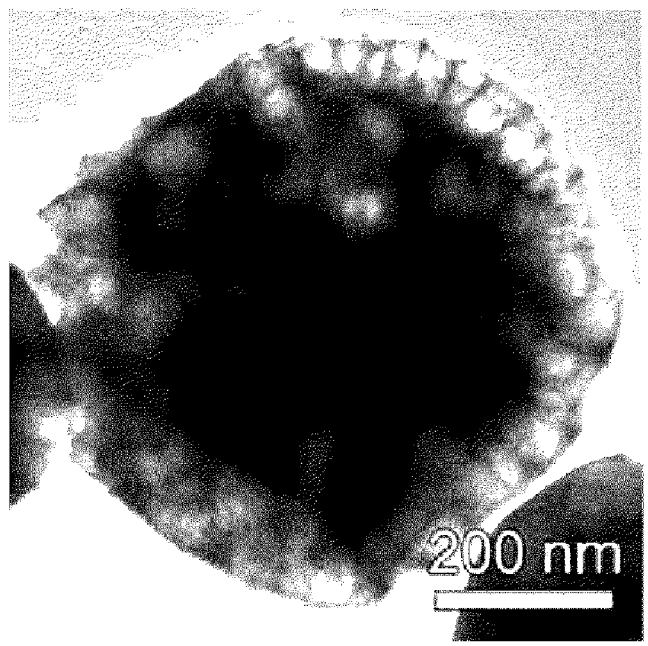

[Fig. 3c]
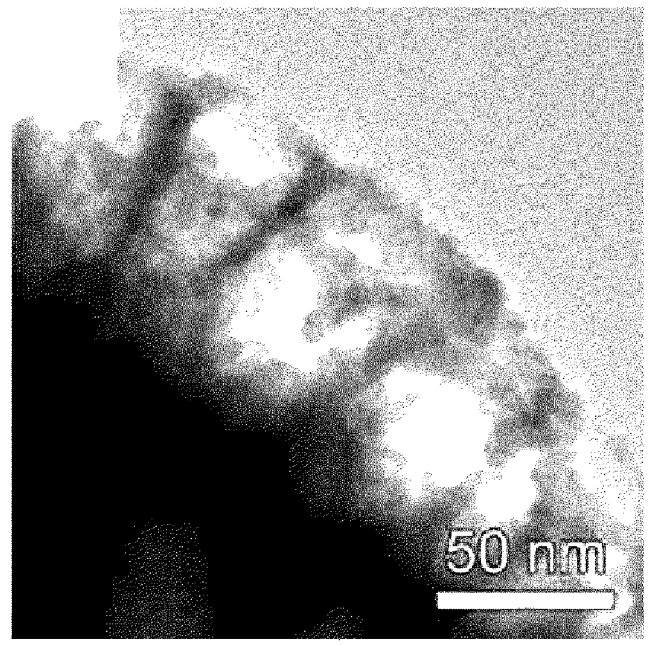
[Fig. 4a]
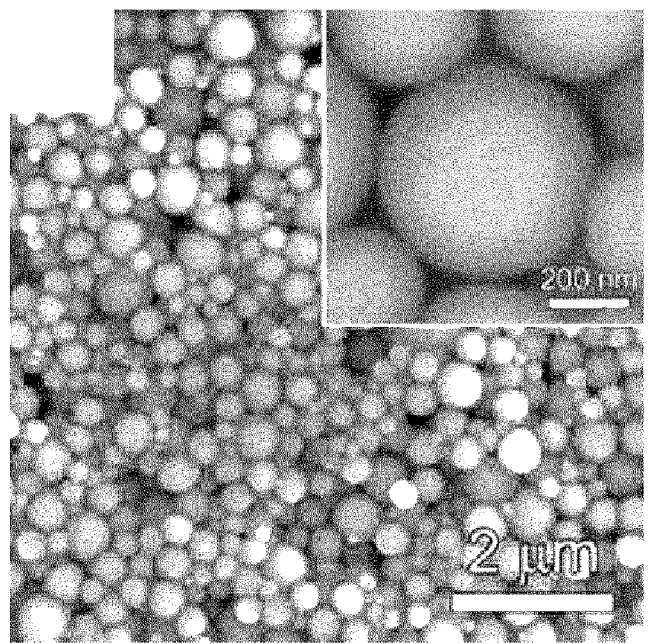

[Fig. 4b]
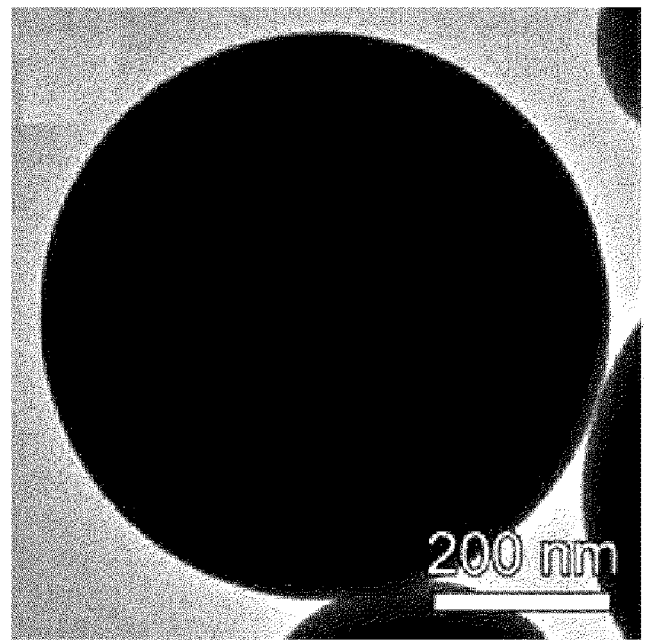
[Fig. 4c]
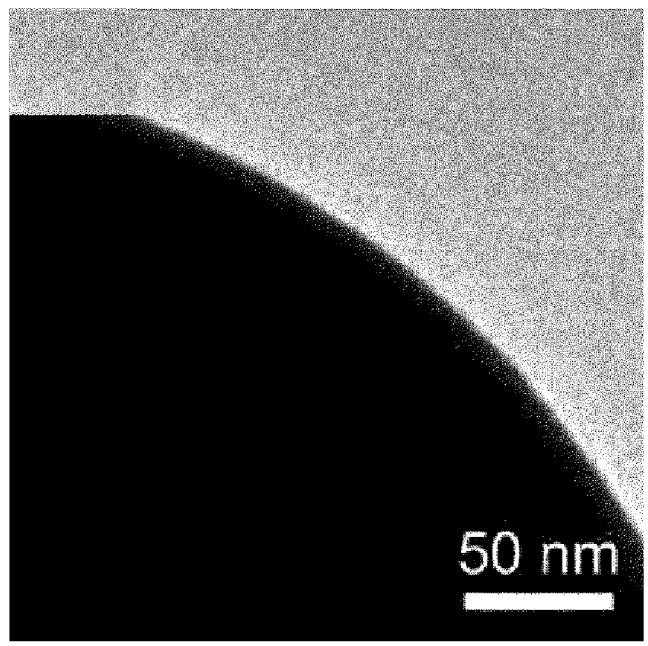

[Fig. 4d]
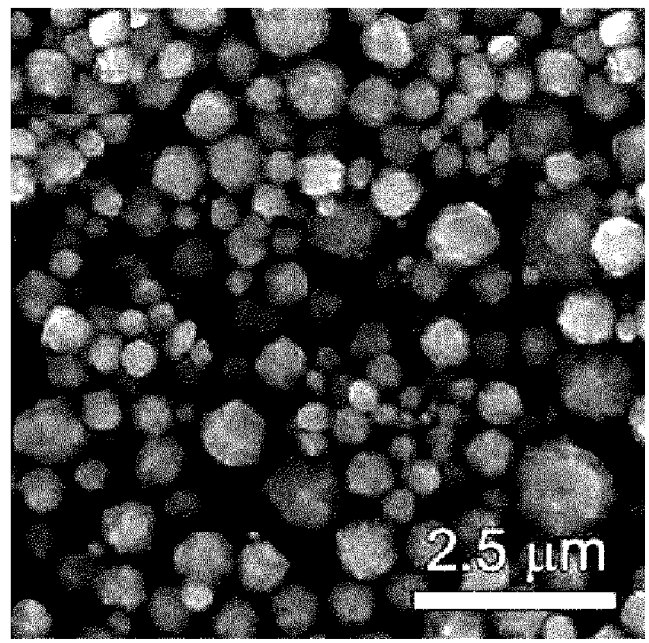
[Fig. 4e]
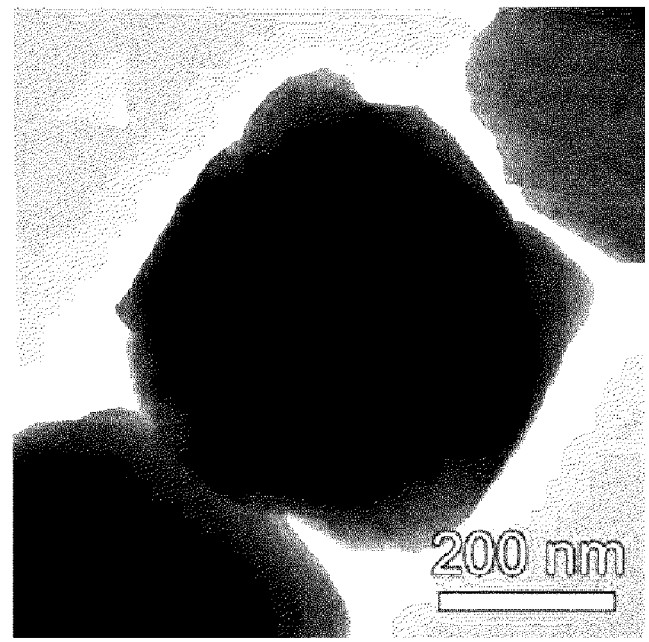

[Fig. 5a]
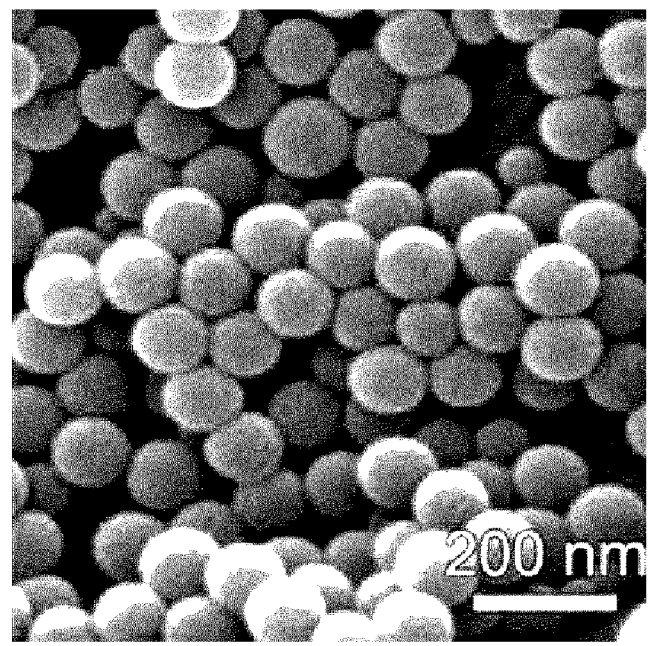
[Fig. 5b]
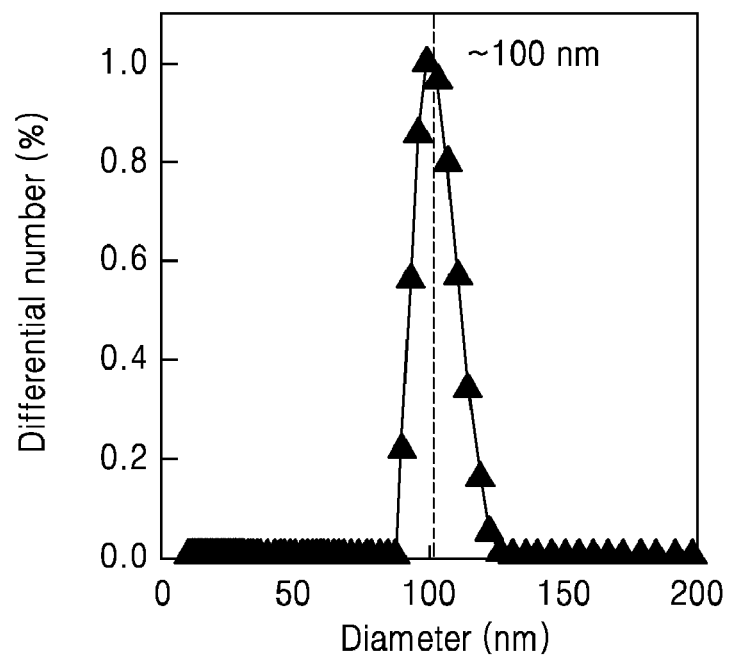

[Fig. 5c]
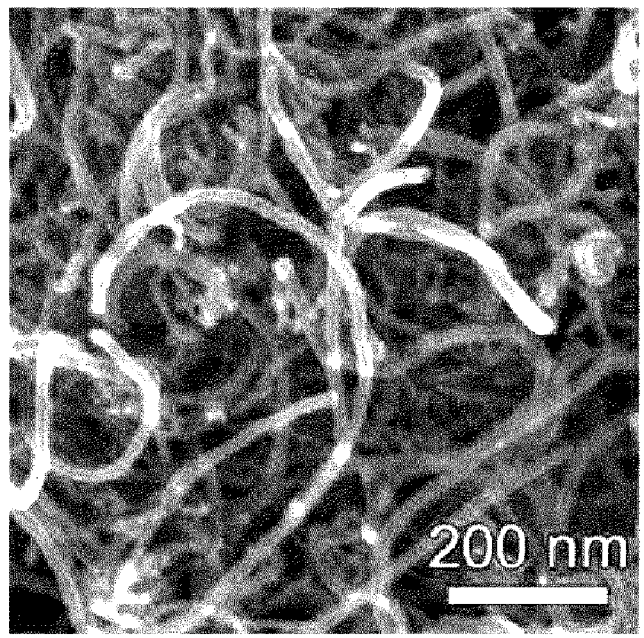

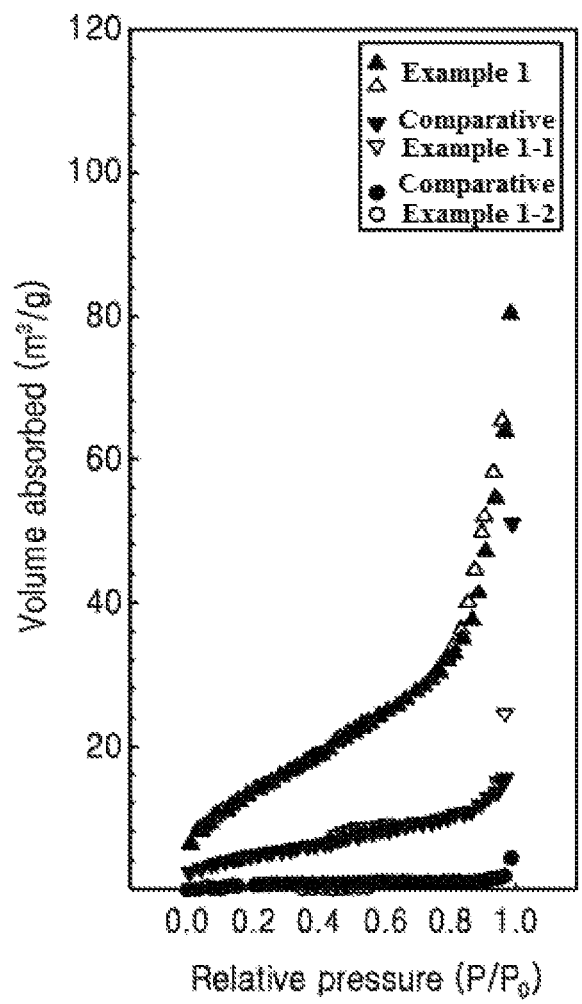
[Fig. 6a]

[Fig. 6b]
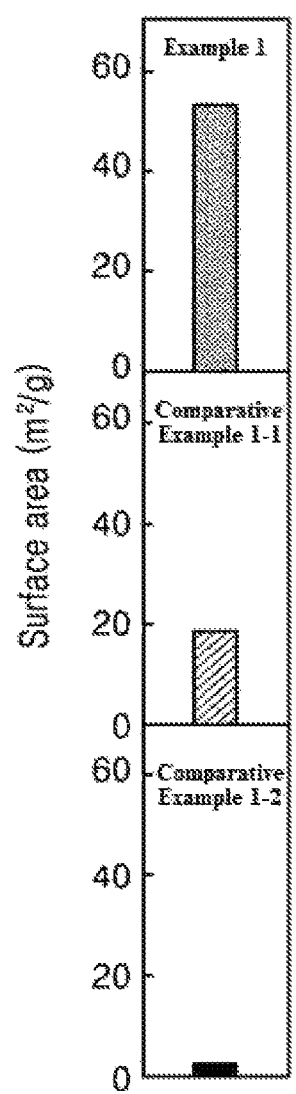

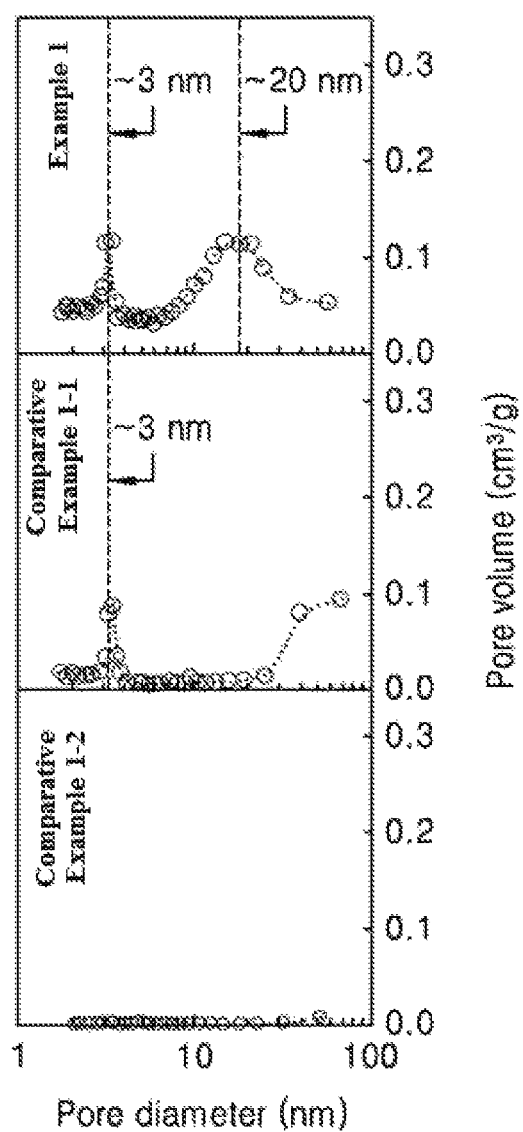
[Fig. 6c]

[Fig. 7a]
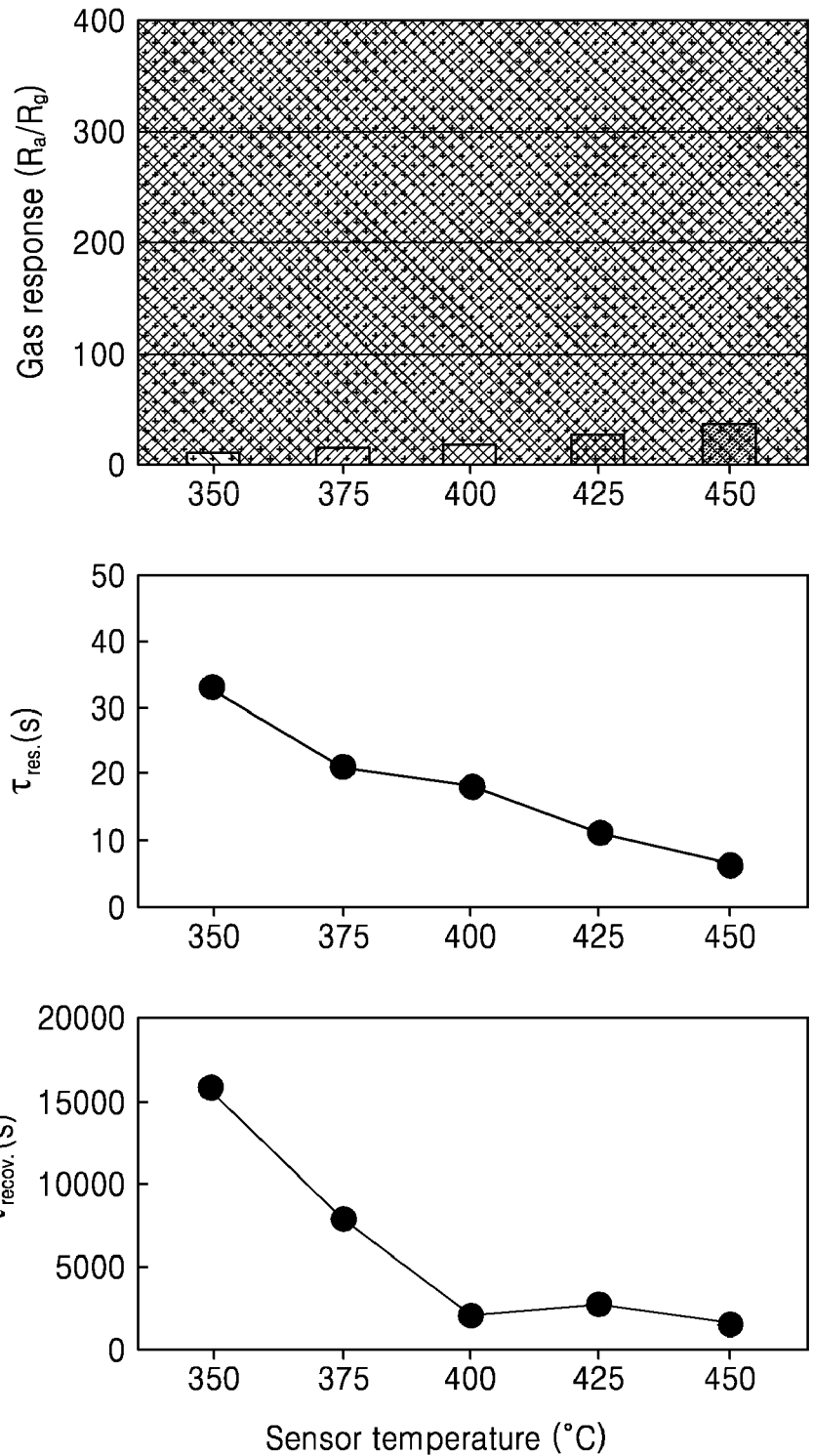

[Fig. 7b]
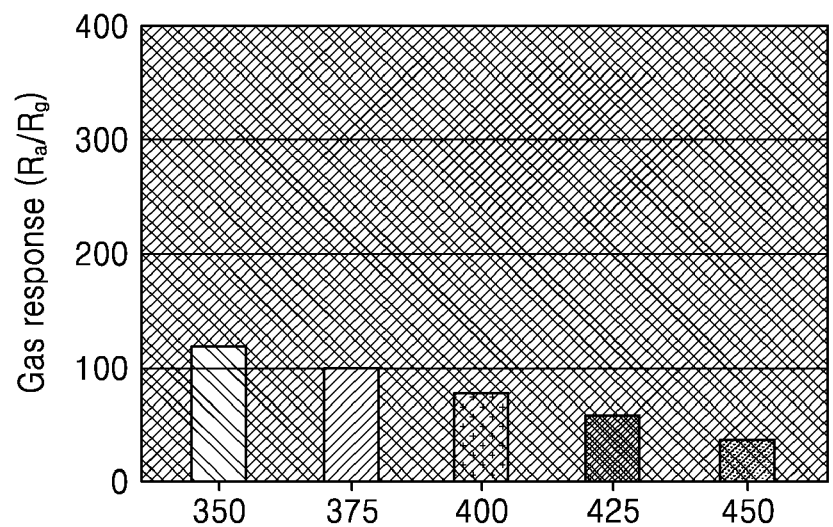
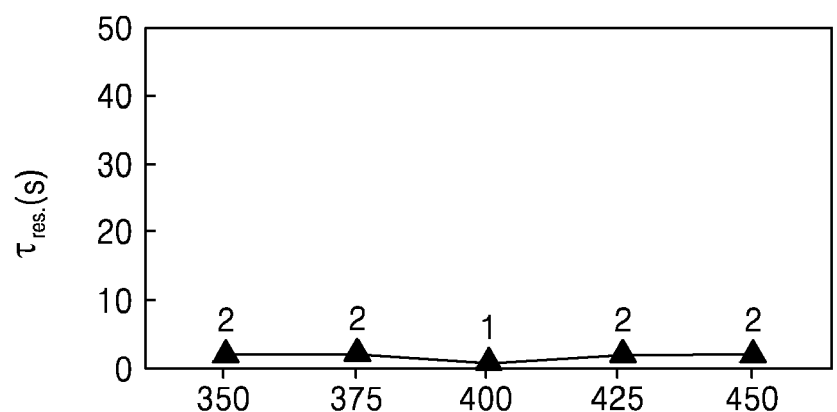
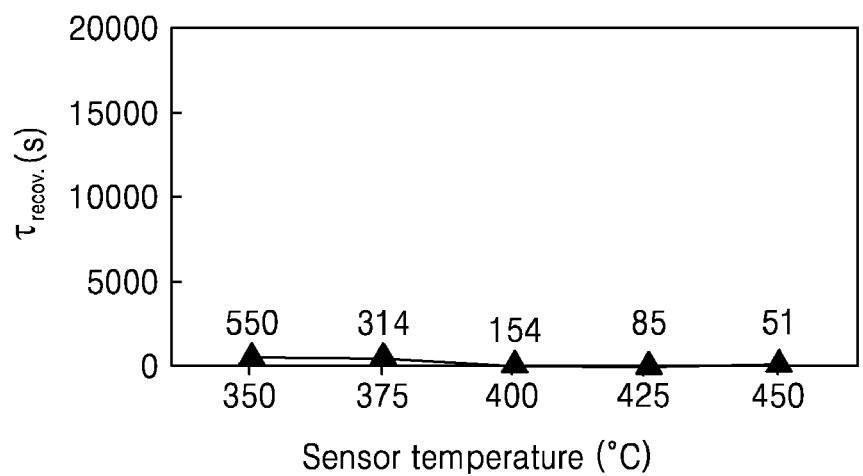

[Fig. 7c]
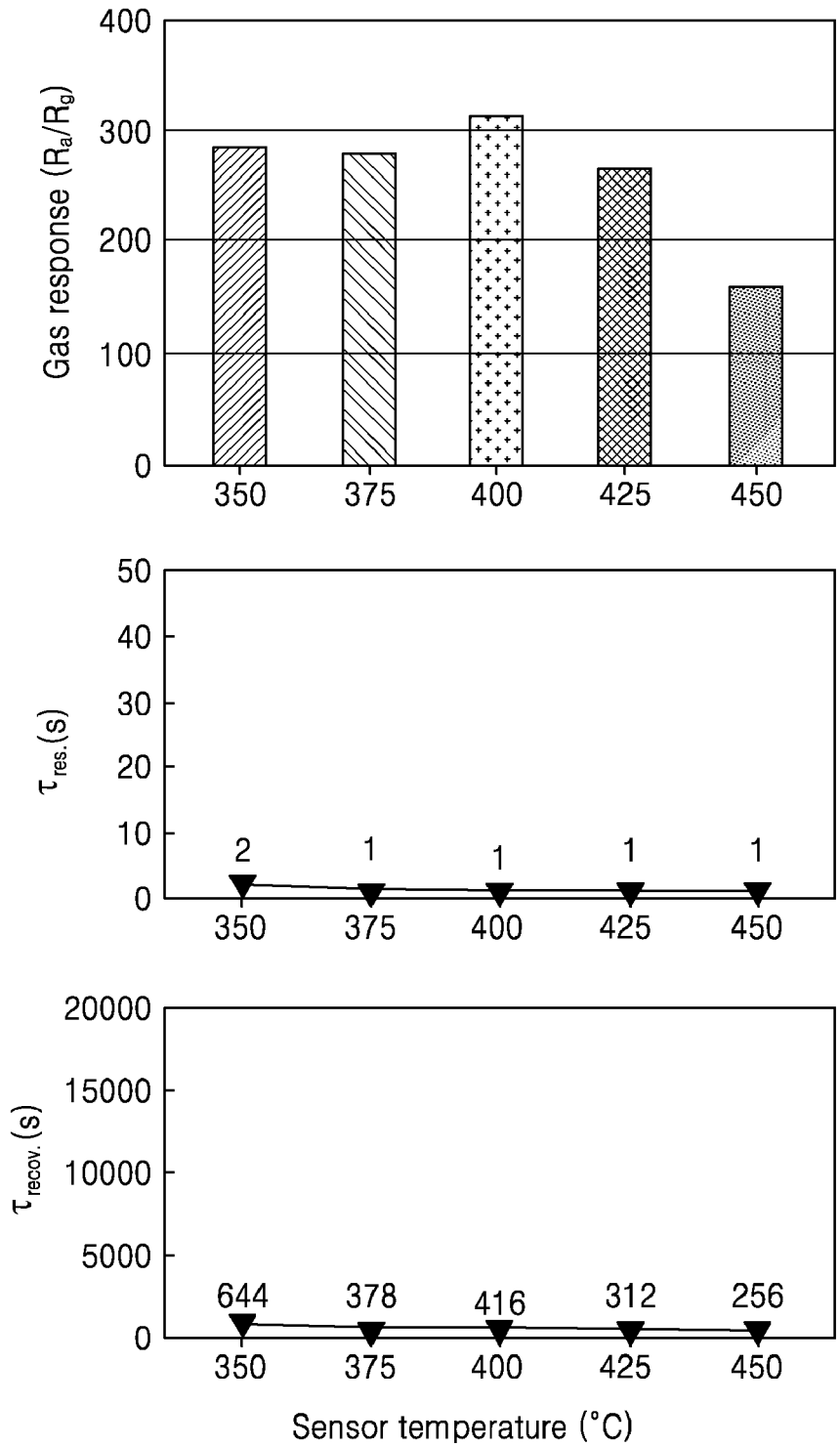

[Fig. 8a]
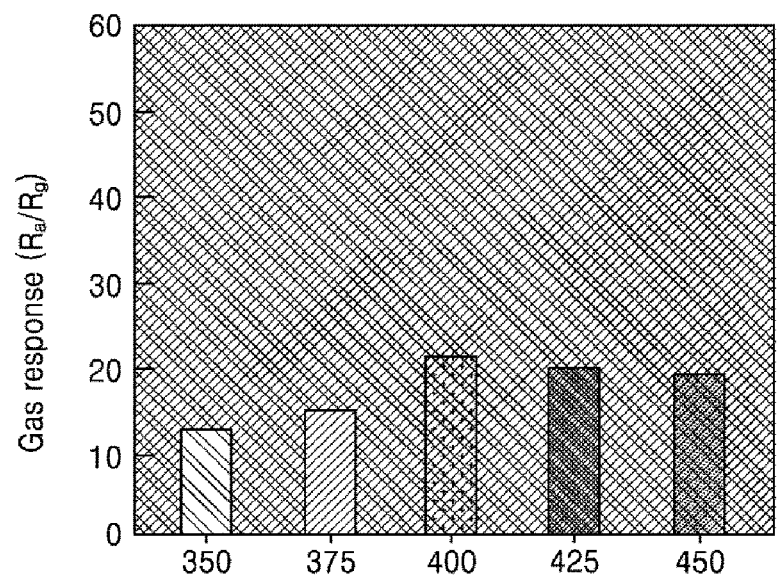
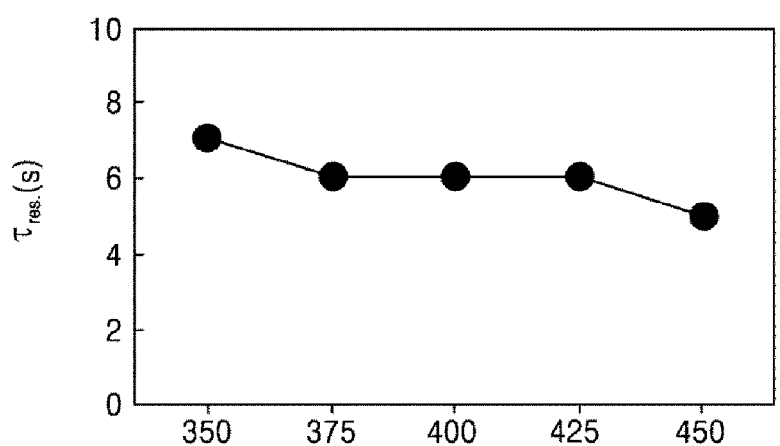
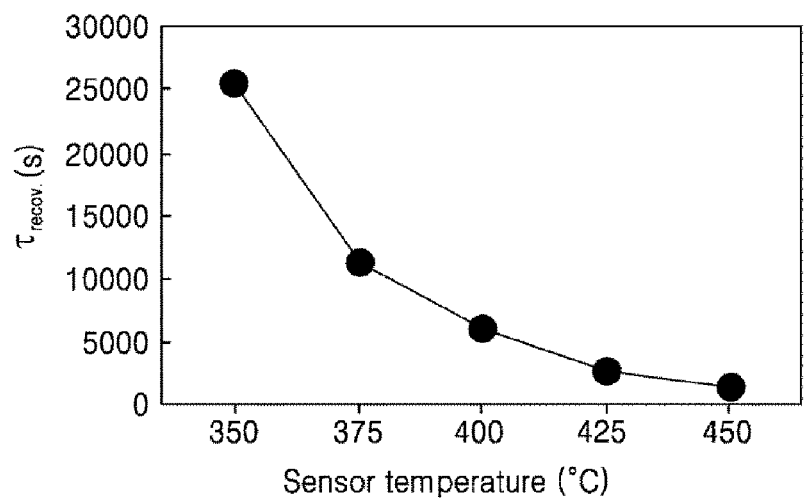

[Fig. 8b]
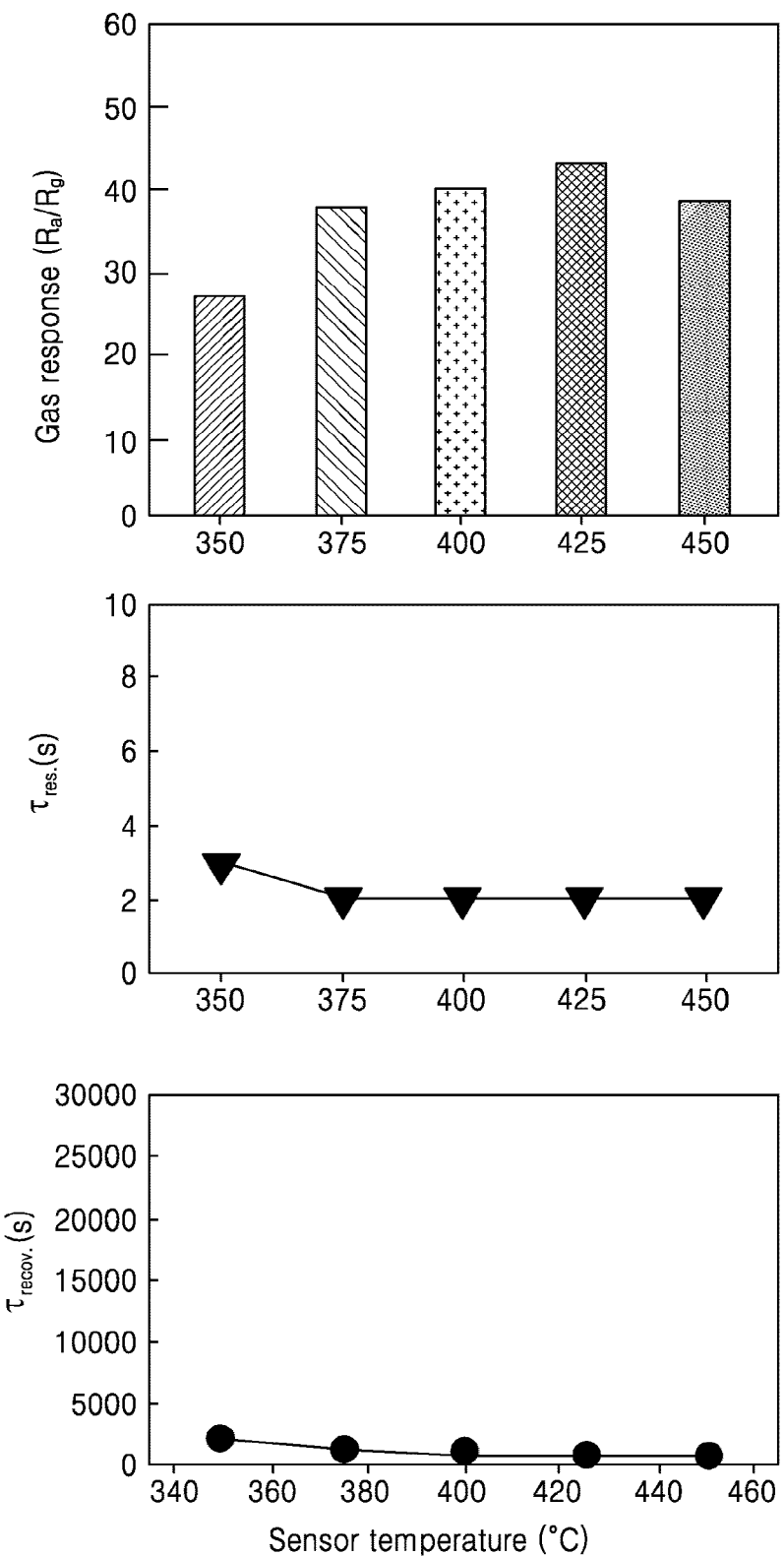

[Fig. 9]
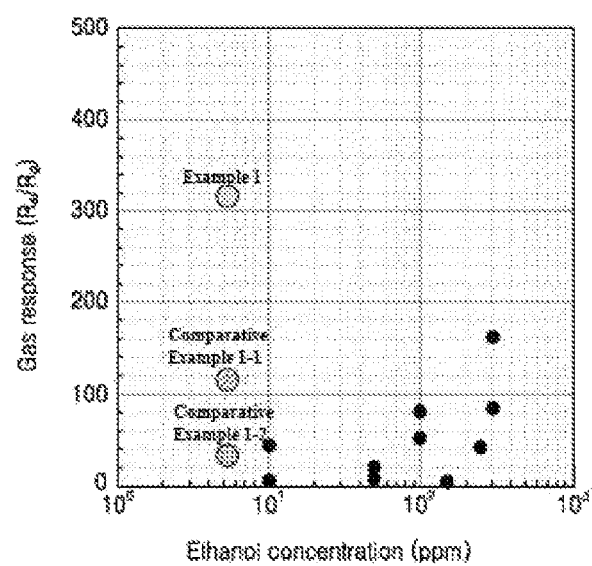

POROUS OXIDE SEMICONDUCTOR INCLUDING THREE-DIMENSIONALLY INTERCONNECTED NANOPORES, MESOPORES, AND MACROPORES, METHOD FOR PREPARING THE POROUS OXIDE SEMICONDUCTOR AND GAS SENSOR INCLUDING THE POROUS OXIDE SEMICONDUCTOR AS GAS SENSING MATERIAL

TECHNICAL FIELD

The present invention relates to a porous oxide semiconductor including three-dimensionally interconnected nanopores, mesopores, and macropores, a method for preparing the porous oxide semiconductor, and a gas sensor including the porous oxide semiconductor as a gas sensing material.

BACKGROUND ART

Semiconductor gas sensors have been widely used in various applications such as measurement of drivers' blood alcohol levels, detection of explosive gases, detection of exhaust gases from automobiles, and detection of toxic industrial gases due to their advantages of high sensitivity, miniaturization, integration, simple operating circuits, and economical prices. With the recent advances in high-tech industries and growing interest in human health and environmental pollution, there has been a rapidly increasing demand for gas sensors for the detection of indoor/outdoor environmental gases, gas sensors for self-diagnosis of diseases, and high-performance artificial olfactory sensors mountable on mobile devices. Thus, there is also a rapidly growing need for oxide semiconductor gas sensors that are highly sensitive and fast respond to very low concentrations of analyte gases.

A remarkable improvement in the sensitivity of gas sensors is a main requirement for accurate detection of very low concentrations of harmful gases, explosive gases, and environmental gases. The operating principle of a gas sensor depends on changes in charge concentration in an oxide semiconductor through interaction between an analyte gas and the surface of the oxide semiconductor. Under these circumstances, three possible approaches are suggested to improve the sensitivity of gas sensors: (1) an approach to maximize gas adsorption by using nanoparticles with high surface area/volume ratio; (2) an approach to increase the proportion of electron depletion layers (in the case of n-type semiconductors) or hole accumulation layers (in the case of p-type semiconductors) present around the surface using nanoparticles; and (3) an approach to design a nanoporous structure of a sensing material such that an analyte gas can be supplied over the entire surface of the sensing material.

For the approaches (1) and (2), it is particularly advantageous to use nanoparticles whose size is on the order of several nanometers (nm). However, in very small nanoparticles, the Van der Waals attractive force increases considerably in inverse proportion to the particle size, and as a result, most of the nanoparticles tend to form dense secondary agglomerates. Thus, gas sensing reactions occur at or near the surface of the secondary particles and gas diffusion into the inner part of the secondary particles requires a long time, making it difficult to obtain high sensitivity and leading to very slow sensing.

In this connection, a porous gas sensing unit of a semiconductor gas sensor and a production method thereof are known (Patent Document 1). According to this method, an alumina slurry is coated on a polyurethane sponge and sintered to prepare a porous alumina ceramic from which the polyurethane sponge is removed, and a paste of a $SnO_2$-based compound as a gas sensing material is coated and dried thereon to produce the porous gas sensing unit. A gas sensor including a gas sensing layer composed of $In_2O_3$ having a nanoporous hollow structure or nanoporous hierarchical structure and a method for fabricating the gas sensor was reported (Patent Document 2). Further, according to a method described in Patent Document 3, nanoporous tin oxide nanotubes are prepared by coating anodic aluminum oxide templates with a surfactant containing amine groups, filling tin oxide/titanium oxide nanoparticles having carboxyl groups in the templates, inducing the formation of peptide bonds between the surfactant and the nanoparticles, followed by a serious of subsequent processing steps, such as removal and sintering of remaining nanoparticles, coating with an electrode material, and etching. Furthermore, many research groups have reported various techniques for synthesizing nano-hierarchical structures and have proposed the fabrication of high-performance gas sensors using the nano-hierarchical structures that permit smooth entrance and exit of gas and have large specific surface areas (Non-Patent Document 1).

In attempts to increase the sensitivity of oxide semiconductor gas sensors, numerous studies have been conducted to increase the access of analyte gas to nanostructures. For example, nanostructures such as nanoparticles, nanowires, nanorods, nanosheets, and nanocubes and nano-hierarchical structures in which the nanostructures are combined and bound to form other types of high-dimensional structures have been investigated as sensing materials (Non-Patent Documents 2-5). Particularly, nano-hierarchical structures reported in Non-Patent Document 1 are advantageous for use in gas sensors because they have many pores for high gas accessibility while maintaining their large specific surface areas.

However, most of the conventional techniques are associated with the preparation of nanostructures by hydrothermal synthesis or solvothermal synthesis of solutions of raw material salts and the fabrication of gas sensors based on pores naturally formed in the course of the preparation of the nanostructures. Accordingly, it is impossible to control the size and shape of the basic nanostructures and the pore size, shape, and volume of the nanostructure-bound states because nucleation, nanostructure growth, and self-assembly between the nanostructures occur naturally in solutions at high temperature and high pressure.

Independent and accurate control of nano-, meso-, and macro-scale pores is of great importance for the design of gas sensors because the diffusion mechanisms of analyte gas are very sensitively dependent on the size, distribution, volume, etc. of pores. For example, surface diffusion becomes dominant in nanopores having a size of several nm, Knudsen diffusion considering collisions of gas with the outer walls of pores occurs in meso-scale pores having a size of ~5-50 nm, and normal diffusion considering only collisions between gas molecules occurs in macropores whose pore size is 100 nm or more (Non-Patent Documents 6 and 7).

There is thus an urgent need to develop a technique for directly and elaborately designing the type, size, and density of pores in sensing materials that have a direct influence on the improvement of gas sensing characteristics and simultaneously functionalizing the sensing materials with pores of different sizes, achieving ultra-high sensitivity to analyte gas.

Patent Document 1: Korean Patent Publication No. 10-2003-0003164
Patent Document 2: Korean Patent Publication No. 10-2010-0025401
Patent Document 3: Korean Patent Publication No. 10-2011-0115896
Non-Patent Document 1: J.-H. Lee, Sens. Actuators B 140 (2009) 319-336
Non-Patent Document 2: H. Zhang, 17 (2007) 2766-2771
Non-Patent Document 3: Q. Dong, Nanotechnology 17 (2006) 3968-3972
Non-Patent Document 4: P. Sun, Sens. Actuators B 173 (2012) 52-57
Non-Patent Document 5: W. Guo, Sens. Actuators B 166-167 (2012) 492-499
Non-Patent Document 6: M. Tiemann, Chem. Eur. J. 13 (2007) 8376-8388
Non-Patent Document 7: T. Wagner, Chem. Soc. Rev. 42 (2013) 4036-4053

SUMMARY OF THE INVENTION

Therefore, the present invention intends to provide a gas sensor which includes a porous oxide semiconductor including three-dimensionally interconnected nanopores, mesopores, and macropores as a material for a gas sensing layer, achieving ultrahigh sensitivity and fast response.

One aspect of the present invention provides a porous oxide semiconductor including three-dimensionally interconnected nanopores, mesopores, and macropores wherein the nanopores have a diameter of 1 nm to less than 4 nm, the mesopores have a diameter of 4 nm to 50 nm, and the macropores have a diameter of 100 nm to less than 1 μm.

According to one embodiment of the present invention, the oxide semiconductor may be selected from the group consisting of $SnO_2$, $WO_3$, $In_2O_3$, $ZnO$, $TiO_2$, $Fe_2O_3$, $MoO_3$, $CuO$, $NiO$, $Co_3O_4$, and $Cr_2O_3$.

A further aspect of the present invention provides a method for preparing a porous oxide semiconductor including: preparing a metal salt solution; dispersing spherical particles and carbon precursors in the metal salt solution, followed by ultrasonic spray to prepare microdroplets; and thermally decomposing the droplets.

According to one embodiment of the present invention, the metal salt solution may be a solution of at least one metal salt of a metal selected from the group consisting of Sn, W, In, Zn, Ti, Fe, Mo, Cu, Ni, Co, and Cr.

According to a further embodiment of the present invention, the spherical template particles may have a diameter of 100 nm to less than 1 μm.

According to another embodiment of the present invention, the spherical template particles may be particles of at least one polymer selected from the group consisting of polystyrene, polymethyl methacrylate, polypropylene, polyvinyl chloride, polyvinylidene fluoride, and polycarbonate.

According to another embodiment of the present invention, the spherical template particles may be carbon spheres produced by hydrothermal synthesis.

According to another embodiment of the present invention, the elongated carbon precursors may be rod-like with a diameter of 4 nm to 50 nm.

According to another embodiment of the present invention, the elongated carbon precursors may be single-walled or multi-walled carbon nanotubes, carbon nanofibers or mixtures thereof.

According to another embodiment of the present invention, the droplets are subjected to primary thermal decomposition in a reaction furnace at 300° C. to 1200° C. for 3 seconds to 100 seconds to burn the spherical template particles and are subsequently subjected to secondary thermal decomposition in a reaction furnace at 500° C. to 1000° C. for 0.5 hours to 10 hours to burn the elongated carbon precursors.

Another aspect of the present invention provides a gas sensor including the porous oxide semiconductor as a material for a gas sensing layer.

BRIEF DESCRIPTION OF THE DRAWINGS

FIG. 1 is a flow chart schematically illustrating a method for preparing a porous oxide semiconductor according to the present invention.

FIGS. 2a, 2b, 2c, 2d and 2e are SEM (2a) and TEM images (2b and 2c) of porous $SnO_2$ as a porous oxide semiconductor prepared in Example 1 and SEM (2d) and TEM images (2e) of porous $WO_3$ as a porous oxide semiconductor prepared in Example 2.

FIGS. 3a, 3b and 3c are SEM (3a) and TEM images (3b and 3c) of porous $SnO_2$ prepared in Comparative Example 1-1.

FIGS. 4a, 4b, 4c 4d and 4e are SEM (4a) and TEM images (4b and 4c) of dense $SnO_2$ prepared in Comparative Example 1-2 and SEM (4d) and TEM images (4e) of dense $WO_3$ prepared in Comparative Example 2.

FIGS. 5a, 5b and 5c show a SEM image (5a) of polystyrene spheres used in the preparation of a porous oxide semiconductor, particle diameter distribution (5b) of the spheres, and a SEM image (5c) of multi-walled carbon nanotubes.

FIGS. 6a, 6b and 6c show changes in volume adsorbed (6a) as a function of relative pressure, specific surface areas (6b), and pore distributions (6c) of oxide semiconductors prepared in Example 1 and Comparative Examples 1-1 and 1-2.

FIGS. 7a, 7b and 7c show the gas responses, response times, and recovery times of oxide semiconductors prepared in Comparative Example 1-2 (7a), Comparative Example 1-1 (7b), and Example 1 (7c) when exposed to 5 ppm of ethanol.

FIGS. 8a and 8b show the gas responses, response times, and recovery times of oxide semiconductors prepared in Comparative Example 2 (8a) and Example 2 (8b) when exposed to 5 ppm of TMA.

FIG. 9 compares the gas responses of a porous oxide semiconductor prepared in Example 1 with those of porous oxide semiconductors prepared in Comparative Examples 1-1 and 1-2 and other known materials.

DETAILED DESCRIPTION OF THE INVENTION

The oxide semiconductor gas sensor of the present invention exhibits ultrahigh sensitivity and ultrafast response to various analyte gases due to the presence of controlled nanopores, mesopores, and macropores.

The present invention will now be described in more detail.

The present inventors have conducted research aimed at providing an oxide semiconductor gas sensor that is highly sensitive and fast responds to a very low concentration of an analyte gas. To this end, the present inventors have intended to effectively design a nanoporous structure of a sensing material such that an analyte gas can be supplied over the entire surface of the sensing material. Particularly, the present inventors have found that when a sensing material is elaborately designed and functionalized such that nanopores, mesopores, and macropores are three-dimensionally interconnected with one another, a gas sensor including the sensing material achieves outstanding sensitivity and fast response compared to conventional gas sensors using nanoporous structures.

The present invention provides a porous oxide semiconductor including three-dimensionally interconnected nanopores, mesopores, and macropores wherein the nanopores have a diameter of 1 nm to less than 4 nm, the mesopores have a diameter of 4 nm to 50 nm, and the macropores have a diameter of 100 nm to less than 1 μm.

The three-dimensionally interconnected structure of the porous oxide semiconductor according to the present invention and the defined sizes of the nanopores, mesopores, and macropores ensure good connectivity between the pores. Therefore, when the porous oxide semiconductor of the present invention is employed in a gas sensing layer of a gas sensor, an entering analyte gas can rapidly and readily diffuse into the gas sensing material. Due to this optimal structure, the gas sensing material can substantially participate in gas sensing.

Particularly, the addition of the one-dimensional mesopores is effective in achieving ultrahigh sensitivity because the use of only the macropores and the nanopores is not sufficient to rapidly diffuse an analyte gas through the nanostructure and the pores with various sizes can be well three-dimensionally interconnected with one another by the presence of the mesopores. The three-dimensional interconnection of the nanopores, mesopores, and macropores and the functionalization with the pores can achieve high sensor sensitivity and markedly improved response/recovery rates.

The porous oxide semiconductor of the present invention can be used without limitation in detecting various kinds of analyte gases. The porous oxide semiconductor of the present invention may be of n-type or p-type depending on the kind of analyte gas. Examples of such n-type oxide semiconductors include $SnO_2$, $WO_3$, $In_2O_3$, ZnO, $TiO_2$, $Fe_2O_3$, and $MoO_3$. Examples of such p-type oxide semiconductors include CuO, NiO, $Co_3O_4$, and $Cr_2O_3$.

The present invention also provides a method for preparing the porous oxide semiconductor. Specifically, the method of the present invention includes: preparing a metal salt solution; dispersing spherical particles and carbon precursors in the metal salt solution, followed by ultrasonic spray to prepare microdroplets; and pyrolyzing the droplets.

FIG. 1 is a flow chart schematically illustrating the method of the present invention. Referring to FIG. 1, first, a dispersion of a metal salt precursor, spherical particles, and carbon precursors is prepared (S1).

The metal salt solution may be a solution of at least one metal salt selected from the group consisting of Sn, W, In, Zn, Ti, Fe, Mo, Cu, Ni, Co, and Cr salts. The kind of the metal salt may vary depending on the kind of a target analyte gas.

The spherical template particles dispersed in the metal salt solution are added to form macropores in the porous oxide semiconductor. The spherical template particles may have a diameter of 100 nm to less than 1 μm. The spherical template particles may be particles of at least one polymer selected from the group consisting of polystyrene, polymethyl methacrylate, polypropylene, polyvinyl chloride, polyvinylidene fluoride, and polycarbonate, which can be synthesized with various sizes. Alternatively, the spherical template particles may be carbon spheres produced by hydrothermal synthesis.

The elongated carbon precursors dispersed in the metal salt solution are added to form mesopores in the porous oxide semiconductor. The elongated carbon precursors may be rod-like with a diameter of 4 nm to 50 nm. Specifically, the elongated carbon precursors may be single-walled or multi-walled carbon nanotubes, carbon nanofibers or mixtures thereof. Particularly, the elongated carbon precursors may be carbon nanofibers having various diameters produced by electrospinning.

Gas generated upon pyrolysis of the carbon precursors is released to form nanopores in the porous oxide semiconductor. The release rate of the gas can be controlled by varying the heating rate during pyrolysis, enabling control over the size and distribution of the nanopores.

The metal salt solution is ultrasonically sprayed to form droplets (S2) and the droplets are thermally decomposed (S3). Specifically, the droplets are subjected to primary thermal decomposition in a reaction furnace at 300° C. to 1200° C. for 3 seconds to 100 seconds to burn the spherical particles. Subsequently, the droplets are subjected to second thermal decomposition in a reaction furnace at 500° C. to 1000° C. for 0.5 hours to 10 hours to burn the carbon precursors. The size and distribution of the nanopores can be controlled by appropriately varying the thermal decomposition temperatures and times.

The porous oxide semiconductor is dispersed in a liquid and is then coated on an electrode overlying a substrate by a suitable coating technique known in the art to form a gas sensing layer, completing the fabrication of a gas sensor (S4).

MODE FOR CARRYING OUT THE INVENTION

The present invention will be explained in more detail with reference to the following examples. These examples are provided to assist in understanding the invention and are not intended to limit the scope of the invention.

Example 1: Fabrication of Gas Sensor Using Porous $SnO_2$ Including Three-Dimensionally Interconnected Nanopores, Mesopores, and Macropores as Material for Gas Sensing Layer A small amount of hydrogen peroxide ($H_2O_2$, 30%, Sigma-Aldrich, USA) was added to 250 ml of triple-distilled water and 1.7 g of stannous oxalate ($C_2O_4Sn$, 98%, Sigma-Aldrich, USA) was added thereto. The mixture was stirred for 30 min to prepare a transparent solution. 3 g of polystyrene (PS) spherical particles (diameter: 100 nm) and 1 mg/mL multi-walled carbon nanotubes (MWCNTs, diameter: 30 nm) treated with sulfuric acid were dispersed in the transparent solution, followed by ultrasonic spray to form microdroplets. The microdroplets were transferred at a flow rate of 5 L/min (argon) to a reaction furnace at 700° C., converted into $SnO_2$/carbon/CNT precursors, and collected in a Teflon-made bag filter. At that time, most of the PS particles were completely decomposed to form macropores but most of the CNTs remained undecomposed in the precursors. The $SnO_2$/carbon/CNT precursors were annealed at 600° C. for 3 h to burn and oxidize remaining carbon and MWCNTs, giving a fine powder of porous spherical $SnO_2$ including three-dimensionally interconnected nanopores, mesopores, and macropores. The reason why the carbon and MWCNTs were burnt at the annealing temperature (600° C.) lower than the ultrasonic spray pyrolysis temperature (700° C.) was that the annealing time (3 h) was much longer than the spray pyrolysis time 15 sec).

The fine powder was mixed with deionized water, dropped onto an alumina substrate where an Au electrode was disposed, and annealed at 550° C. for 2 h to fabricate a gas sensor. Changes in the resistance of the sensor were measured while alternately feeding pure air or air+gas at 350-450° C. The gas was previously mixed and their concentration was rapidly changed using a 4-way valve. The total gas flow rate was fixed to 500 SCCM such that no temperature difference was induced when the gas concentration was changed.

Example 2: Fabrication of Gas Sensor Using Porous $WO_3$ Including Three-Dimensionally Interconnected Nanopores, Mesopores, and Macropores as Material for Gas Sensing Layer 1.294 g of ammonium metatungstate hydrate (99.99%, Sigma-Aldrich, USA) was added to 250 ml of triple-distilled water. The mixture was stirred for ~1 day to prepare a transparent solution. 3 g of PS (diameter: 100 nm) and 0.5 mg/mL MWCNTs (diameter: 30 nm) treated with sulfuric acid were dispersed in the transparent solution, followed by ultrasonic spray to form microdroplets. The microdroplets were transferred at a flow rate of 5 L/min (argon) to a reaction furnace at 700° C., converted into $WO_3$/carbon/CNT precursors, and collected in a Teflon-made bag filter. The $WO_3$/carbon/CNT precursors were annealed at 550° C. for 3 h, giving a fine powder of porous spherical $WO_3$ including three-dimensionally interconnected nanopores, mesopores, and macropores. The fine powder was mixed with deionized water, dropped onto an alumina substrate where an Au electrode was disposed, and annealed at 500° C. for 2 h to fabricate a gas sensor. Thereafter, the gas sensing characteristics of the sensor were measured in the same manner as in Example 1.

Comparative Example 1-1: Fabrication of Gas Sensor Using Porous $SnO_2$ Including Nanopores and Macropores as Material for Gas Sensing Layer A small amount of hydrogen peroxide ($H_2O_2$, 30%, Sigma-Aldrich, USA) was added to 250 ml of triple-distilled water and 1.7 g of stannous oxalate ($C_2O_4Sn$, 98%, Sigma-Aldrich, USA) was added thereto. The mixture was stirred for 30 min to prepare a transparent solution. 3 g of PS (diameter: 100 nm) was dispersed in the transparent solution, followed by ultrasonic spray to form microdroplets. The microdroplets were transferred at a flow rate of 5 L/min (argon) to a reaction furnace at 700° C., converted into $SnO_2$/carbon precursors, and collected in a Teflon-made bag filter. The $SnO_2$/carbon precursors were annealed at 600° C. for 3 h, giving a fine powder of porous spherical $SnO_2$ including nanopores and macropores. Thereafter, a gas sensor was fabricated and its gas sensing characteristics were measured in the same manner as in Example 1.

Comparative Example 1-2: Fabrication of Gas Sensor Including Dense Spherical $SnO_2$ Consisting of Fine Powders A small amount of hydrogen peroxide ($H_2O_2$, 30%, Sigma-Aldrich, USA) was added to 250 ml of triple-distilled water and 1.7 g of stannous oxalate ($C_2O_4Sn$, 98%, Sigma-Aldrich, USA) was added thereto. The mixture was stirred for 30 min to prepare a transparent solution. Then, the transparent solution was ultrasonically sprayed to form microdroplets. The microdroplets were transferred at a flow rate of 5 L/min (argon) to a reaction furnace at 700° C., converted into $SnO_2$ precursors, and collected in a Teflon-made bag filter. The $SnO_2$ precursors were annealed at 600° C. for 3 h, giving sense spherical $SnO_2$ consisting of fine powders. Thereafter, a gas sensor was fabricated and its gas sensing characteristics were measured in the same manner as in Example 1.

Comparative Example 2: Fabrication of Gas Sensor Including Dense Spherical $WO_3$ Consisting of Fine Powders 1.294 g of ammonium metatugnstate hydrate (99.99%, Sigma-Aldrich, USA) was added to 250 ml of triple-distilled water. The mixture was stirred for ~1 day to prepare a transparent solution. Then, the transparent solution was ultrasonically sprayed to form microdroplets. The microdroplets were transferred at a flow rate of 5 L/min (argon) to a reaction furnace at 700° C., converted into $WO_3$ precursors, and collected in a Teflon-made bag filter. The $WO_3$ precursors were annealed at 550° C. for 3 h, giving a dense spherical $WO_3$ consisting of fine powders. Thereafter, the fine powder was mixed with deionized water, dropped onto an alumina substrate where an Au electrode was disposed, and annealed at 500° C. for 2 h to fabricate a gas sensor. The gas sensing characteristics of the gas sensor were measured in the same manner as in Example 1.

The resistances of the gas sensors fabricated in Examples 1 and 2 and Comparative Examples 1-1, 1-2, and 2 to reducing gases were measured in all temperature zones. As a result, the gas sensors were found to exhibit n-type semiconductor characteristics because their resistances were decreased in all reducing gases.

The gas response of each sensor was defined as $R_a/R_g$ ($R_a$: resistance of the sensor in air, $R_g$: resistance of the sensor in the corresponding gas). When the resistance of each sensor in air was kept constant, the atmosphere was suddenly changed to ethanol or TMA as an analyte gas. Thereafter, when the resistance of the sensor in the analyte gas was kept constant, the atmosphere was suddenly changed to air. At this time, a change in the resistance of the sensor was measured. When the final resistance reached upon exposure to the gas was $R_g$ and the resistance in air was $R_a$, the time at which 90% of the resistance difference ($R_g-R_a$) is changed to reach a point close to the resistance $R_g$ was defined as 90% response time. The resistance $R_g$ increased when the atmosphere was changed to air after exposure to the gas. The time at which 90% of the resistance difference ($R_g-R_a$) is changed to reach a point close to the resistance $R_a$ was defined as 90% recovery time.

Results

FIGS. 2 to 4 are SEM and TEM images of the porous oxide semiconductors synthesized through ultrasonic spray pyrolysis in Example 1 (FIGS. 2a to 2c), Example 2 (FIGS. 2d and 2e), Comparative Example 1-1 (FIGS. 3a to 3c), Comparative Example 1-2 (FIGS. 4a to 4c), and Comparative Example 2 (FIGS. 4d and 4e). Referring to these images, the porous fine powders produced in Examples 1 and 2 had nano-hierarchical structures in which a large number of pores formed as a result of decomposition/oxidation of PS (FIG. 5a) and MWCNTs (FIG. 5b) were present in spherical structures (see FIGS. 2a to 2e). The macropores (size ~100 nm) formed as a result of oxidation of PS could be easily confirmed in the TEM images but the nanopores and mesopores were difficult to directly find in the TEM images. It was also difficult to directly find pores with different sizes from the macropores in the TEM images of the porous oxide semiconductor prepared without MWCNTs in Comparative Example 1-1 but the porous oxide semiconductor of Comparative Example 1-1 had a porous structure with a large specific surface area, like the porous oxide semiconductors of Examples 1 and 2 (see FIGS. 3a to 3c). The SEM and TEM images of the internally dense spherical $SnO_2$ and $WO_3$ prepared in Comparative Examples 1-2 and 2 are shown in FIGS. 4a to 4e. The SEM and TEM analysis results show that the porous gas sensors of Examples 1 and 2 had a large number of pores and good connectivity between the pores. Therefore, entering gases can rapidly and readily diffuse into the gas sensing materials. Due to these optimal structures, the gas sensing materials can substantially participate in gas sensing. The ~100 nm diameter PS spherical particles were used to form spherical macropores (see FIGS. 5a and 5b) and the ~20 nm diameter MWCNTs were used to form mesopores having a size of several tens of nm (see FIG. 5c).

FIGS. 6a to 6c show specific surface areas and pore distributions of the particles prepared in Example 1 and Comparative Examples 1-1 and 1-2, which were analyzed by the BET method. The analysis results show that 20 nm sized mesopores and 3 nm sized nanopores were formed as a result of oxidation of MWCNTs in Example 1 (see the top of FIG. 6c). Here, 100 nm sized pores were difficult to confirm by the limit of detection of the BET method but the corresponding spherical pores (size: 100 nm) were directly confirmed by TEM analysis. The presence of 3 nm sized nanopores in the porous oxide semiconductor of Comparative Example 1-1 was confirmed by pore analysis (see the middle of FIG. 6c), as in the porous oxide semiconductor of Example 1. The nanopores were believed to be formed when gas generated as a result of the PS decomposition was diffused outward inside the spherical structure. The structure of Comparative Example 1-2 was very dense without nanopores, mesopores, and macropores (see the bottom of FIG. 6c).

The presence of a large number of nanopores, mesopores, and macropores in the porous oxide semiconductor of Example 1 is responsible for the large specific surface area (53.2 $m^2 g^{-1}$) of the porous oxide semiconductor (see the top of FIG. 6b). In contrast, the presence of only nanopores and macropores in the porous oxide semiconductor of Comparative Example 1-1 is responsible for the moderate specific surface area (18.4 $m^2 g^{-1}$) of the porous oxide semiconductor (see the middle of FIG. 6b). The dense structure of Comparative Example 1-2 had a very small specific surface area of 2.42 $m^2 g^{-1}$ (see the bottom of FIG. 6b).

FIGS. 7a to 7c show the gas responses to 5 ppm of ethanol and response/recovery times of the gas sensors fabricated in Example 1 (FIG. 7c), Comparative Example 1-1 (FIG. 7b), and Comparative Example 1-2 (FIG. 7a) at operating temperatures of 350-450° C. The gas responses of the gas sensor of Example 1 to 5 ppm of ethanol were found to be very high (158.8-316.5) (see the top of FIG. 7c). The gas sensor of Example 1 showed the highest response (316.5) to 5 ppm of ethanol at 400° C. The response time and recovery time of the gas sensor were 1 sec (see the middle of FIG. 7c) and 416 sec (see the bottom of FIG. 7c) at 400° C., respectively, demonstrating very fast response of the gas sensor.

In contrast, the gas responses of the gas sensor of Comparative Example 1-1 to 5 ppm of ethanol were 32.9-117.6 with the highest response of 117.6 at 350° C. (see the top of FIG. 7b). At that time, the response and recovery times were 2 sec and 550 sec, respectively. The responding speed of the gas sensor of Comparative Example 1-1 was slower than that of the gas sensor of Example 1 but is still considered very fast (see the middle and bottom of FIG. 7b). The dense structure of Comparative Example 1-2 was found to have the highest response (34.2) at 450° C. (see the top of FIG. 7a). The response time and recovery time were 6 sec (see the middle of FIG. 7a) and 1485 sec (see the bottom of FIG. 7a) at 450° C., respectively.

The gas responses of the gas sensor of Example 1 were extraordinarily high despite the absence of a catalyst to increase gas response, indicating that the structure including a large number of nanopores, mesopores, and macropores is very suitable as a gas sensing material.

The gas sensor of Comparative Example 1-1 having 100 nm sized macropores and 3 nm sized nanopores showed high responses compared to the gas sensor of Comparative Example 1-2 having a dense internal structure. This is believed to be because the analyte gas can more effectively reach the surface of the sensing material through the 100 nm sized pores and is supported by the greatly increased sensing rate. The coexistence of not only 100 nm sized macropores and 3 mm sized nanopores but also 20 nm diameter one-dimensional mesopores could achieve ultrahigh response, as in the gas sensor of Example 1. This indicates that the use of only macropores and nanopores is not sufficient to rapidly diffuse the analyte gas through the nanostructure and ultrahigh response and fast response can be achieved only when the pores with various sizes can be well three-dimensionally interconnected with one another. Therefore, it can be concluded that various pore sizes of macropores, mesopores, and nanopores and interconnectivity between the pores are important factors in designing gas sensors with ultrahigh response.

Particularly, Knudsen diffusion occurs in mesopores whose pore size is in the range of several tens of nm and the Knudsen diffusion coefficient is known to be proportional to the size of pores. Accordingly, the diffusion coefficient of pores having a size of 20 nm is 4 times higher than that of pores having a size of 5 nm, which explains the importance of control over the size of mesopores in increasing the diffusion of an analyte gas. It is believed that the additional introduction of 20 nm diameter mesopores in Example 1 results in a 6- to 7-fold increase in the diffusion of the analyte gas compared to the introduction of 3 nm diameter nanopores.

The present invention proposes that the size controllability of nanopores, mesopores, and macropores is an important advantage. The production of PS spherical template particles with various sizes has been well established. For example, the use of PS spherical template particles whose diameter is adjusted to 50-500 nm enables control over the size of macropores. It should be understood that PMMA, PP, PVC, PVDF, and PC spherical template particles can be used instead of PS spherical particles. Carbon spheres with various diameters produced by hydrothermal synthesis can also be used as the precursors. Gas generated upon pyrolysis of the carbon precursors is released to form nanopores in the porous oxide semiconductors. An increased heating rate during pyrolysis leads to rapid gas generation, enabling control over the size and distribution of nanopores.

Finally, the use of carbon nanotubes with various diameters as precursors leads to the formation of 5-50 nm one-dimensional pores after pyrolysis. Single-walled carbon nanotubes and multi-walled carbon nanotubes with various diameters can be utilized as one-dimensional carbon precursors for the formation of mesopores. Particularly, carbon nanofibers with various diameters produced by electrospinning can be utilized as precursors for the formation of one-dimensional mesopores. The porosity of spherical particles can be increased by increasing the amount of the spherical one-dimensional carbon precursors. In addition, pores with three or more different sizes can be reproducibly formed from a mixture of carbon precursors having various sizes and diameters. This suggests that when the sizes and volumes of nanopores, mesopores, and macropores with various sizes and the connectivity between the pores are controlled in an independent and reproducible manner, ultrahigh-performance gas sensors can be designed.

FIGS. 8a and 8b show the responses to 5 ppm of triethylamine (TMA), response times, and recovery times of the gas sensors of Example 2 (FIG. 8b) and Comparative Example 2 (FIG. 8a) at operating temperatures of 350-450° C. $WO_3$ is a representative acidic oxide semiconductor that is known to exhibit high response to the basic gas TMA. The gas responses of the gas sensor of Example 2 to 5 ppm of TMA were found to be 27.2-43.3 at operating temperatures of 350-450° C., with the highest response of 43.3 at 425° C. (see the top of FIG. 8b). The response time and recovery time of the gas sensor were found to be as high as 2 sec (see the middle of FIG. 8b) and 579 sec (see the bottom of FIG. 8b) at 425° C., respectively. In contrast, the gas sensor fabricated using the dense particles in Comparative Example 2 had responses of 12.8-20.1 at operating temperatures of 350-450° C. (see the top of FIG. 8a), which were lower than those of the gas sensor of Example 2. The highest response of the gas sensor of Comparative Example 2 was obtained at 400° C., and the response time and recovery time of the gas sensor were 6 sec (see the middle of FIG. 8a) and 5881 sec (see the bottom of FIG. 8a) at 400° C., respectively, indicating very slow response of the gas sensor. These results demonstrate that functionalization of the sensing material with nanopores, mesopores, and macropores increases the response of the sensor and markedly improves the response/recovery rates of the sensor regardless of the kind of the sensing material. These results show that control of nanopores, mesopores, and macropores in porous oxide semiconductor nanostructures will be a promising approach to design gas sensors with ultrahigh gas response. In conclusion, control of nanopores, mesopores, and macropores in porous nanostructures of n-type oxide semiconductors such as $SnO_2$, $WO_3$, $In_2O_3$, ZnO, $TiO_2$, $Fe_2O_3$, $MoO_3$ and p-type oxide semiconductor such as CuO, NiO, $Co_3O_4$, and $Cr_2O_3$ ensures ultrahigh response of gas sensors.

Finally, the gas response of the gas sensor of Example 1, which was fabricated using spherical $SnO_2$ particles including nanopores, mesopores, and macropores as materials for a gas sensing layer, was compared with those previously reported. The results are shown in FIG. 9. Referring to FIG. 9, the gas response of the gas sensor of Example 1 was much higher than those previously reported and was the highest ever achieved in pure $SnO_2$ gas sensors. In conclusion, according to the present invention, control over nanopores, mesopores, and macropores enables the fabrication of oxide semiconductor gas sensors with ultrahigh response and ultrafast response.

The invention claimed is:

1. A porous oxide semiconductor for gas sensing comprising three-dimensionally interconnected nanopores, mesopores, and macropores wherein the nanopores have a diameter of 1 nm to less than 4 nm, the mesopores have a diameter of 4 nm to 50 nm, and the macropores have a diameter of 100 nm to less than 1 μm, wherein the mesopores are tubular and the macropores are spherical, and wherein the nanopores and the macropores are three-dimensionally interconnected by the mesopores, and wherein the oxide semiconductor is selected from the group consisting of SnO2, WO3, In2O3, ZnO, TiO2, Fe2O3, MoO3, CuO, NiO, Co3O4, and Cr2O3.

2. A gas sensor comprising the porous oxide semiconductor according to claim 1 as a material for a gas sensing layer.

3. The porous oxide semiconductor according to claim 1, wherein the nanopores are spherical.

* * * * *